United States Patent [19]
Watts et al.

[11] Patent Number: 5,437,983
[45] Date of Patent: Aug. 1, 1995

[54] HETEROGENEOUS BINDING ASSAYS

[75] Inventors: Richard P. Watts, Brisbane; Mary C. Ericson, Santa Cruz; Hrair Kirakossian, San Jose; Chiu C. Chang, Sunnyvale, all of Calif.

[73] Assignee: Syntex (U.S.A.) Inc., Palo Alto, Calif.

[21] Appl. No.: 13,116

[22] Filed: Feb. 1, 1993

Related U.S. Application Data

[63] Continuation of Ser. No. 389,452, Aug. 4, 1989, abandoned.

[51] Int. Cl.$^6$ ............... G01N 33/543; G01N 33/546
[52] U.S. Cl. ..................... 435/7.5; 435/7.9; 435/7.92; 435/7.94; 436/518; 436/524; 436/527; 436/531; 436/532; 436/533; 436/534; 436/536; 436/538; 436/540; 436/541; 436/824
[58] Field of Search ............. 435/7.5, 7.9, 7.92, 435/7.94; 436/518, 524, 527, 531, 532, 533, 534, 536, 538, 540, 541, 824

[56] References Cited

U.S. PATENT DOCUMENTS

| | | | |
|---|---|---|---|
| 4,298,685 | 11/1981 | Parikh et al. | 435/7.5 |
| 4,350,760 | 9/1982 | Nicolas et al. | 435/7.92 |
| 4,486,530 | 12/1984 | David et al. | 435/7 |
| 4,656,143 | 4/1987 | Baker et al. | 436/527 |
| 4,659,678 | 4/1987 | Forrest et al. | 436/512 |
| 4,685,480 | 8/1987 | Eck | 141/65 |
| 4,777,145 | 10/1988 | Luotola et al. | 436/526 |
| 4,780,423 | 10/1988 | Bluestein et al. | 436/527 |
| 4,962,047 | 10/1990 | Place | 436/824 X |

FOREIGN PATENT DOCUMENTS

| | | |
|---|---|---|
| 201079 | 11/1986 | European Pat. Off. |
| 0253270 | 1/1988 | European Pat. Off. |
| 0293779 | 12/1988 | European Pat. Off. |
| WO8703690 | 6/1987 | WIPO |

OTHER PUBLICATIONS

Babashak, et al., "Journal of Chromatography", V:444 (188) 21–28.
P. Tijssen et al., "Practice and Theory of Enzyme Immunoassays", pp. 123–125 & 330–337 & 297–298, Elsevier, N.Y., N.Y., 1985.
Maggio et al., "Enzyme Immunoassay", 1980, Boca Raton, Fla., CRC Press, Inc., pp. 169–170.

*Primary Examiner*—Toni R. Scheiner
*Assistant Examiner*—Christopher L. Chi
*Attorney, Agent, or Firm*—Shelley G. Precivale; Linda J. Nyari

[57] ABSTRACT

A method for carrying out a binding assay is described wherein a member of a specific binding pair (sbp) and a sample are combined with a matrix of non-porous beads in a liquid medium under conditions such that the beads bind to the sbp member. The liquid medium is removed from the beads by aspiration using an aspiration tube having one or more orifices each of a diameter smaller than the minimum diameter of the smallest bead thereby allowing removal of the liquid medium while prohibiting aspiration of the beads.

40 Claims, No Drawings

HETEROGENEOUS BINDING ASSAYS

This is a continuation of application Ser. No. 07/389,452, filed Aug. 4, 1989, now abandoned.

BACKGROUND OF THE INVENTION

Heterogeneous binding assays require that a means be provided to separate a labeled binding reagent from an unlabeled binding reagent. Frequently, a surface is provided to which is bound a specific binding ligand or receptor. Various surfaces have been used, such as latex beads, which can be filtered; tubes or wells, usually plastic, which also serve as the container for the assay mixture; magnetic particles which can be separated in a magnetic field gradient; insoluble polymers which are separated by centrifugation or are used as the stationary phase of a chromatograph; bibulous materials such as cellulose or glass paper through which reagents can be filtered or transferred by capillary action.

U.S. Pat. No. 4,659,678 describes a method for carrying out an immunoassay in which the complex is formed in a liquid medium prior to binding to a solid support by the use of one or more monoclonal antibodies. Detection of the bound sample is measured using labeling methods such as labeling with radioactive iodine, and fluorimetric and enzyme labeling.

U.S. Pat. No. 4,780,423 describes a heterogeneous assay using controlled pore glass particles. The controlled pore glass particles are used in a fluorescent immunoassay as the support for the specific binding partner bound to a ligand. As used in the invention, the glass particles bind a complex of interest, the detection of which is achieved by use of a fluorescent probe. Measurement of fluorescence is carried out in the presence of the glass particles.

U.S. Pat. No. 4,298,685 describes the use of biotin-labeled antibodies for the quantitative determination of a biological substance in a test sample. Quantitative measurements of the amount of biological sample present are obtained by the use of an enzyme label, such as horseradish peroxidase, which when bound to the sample can be used as a means to detect the presence of the biological substance in the sample.

The use of solid particles, such as magnetic particles or glass beads, to serve as the support for an immunologic assay is known. An example of such assays include the use of magnetic particles as the solid support in a fluorometric immunoassay as described in U.S. Pat. No. 4,777,145. The use of avidin-coated glass beads in immunoaffinity chromatography and a method for preparing such avidin-coated beads is described by Babashak J. V. and T. M. Phillips, *J. of Chromatography* 444:21 (1988).

The present invention provides a means to carry out the various heterogeneous binding assays using the improved method of the invention so as to achieve high capacity, rapid binding and convenient washing of the stationary phase of the heterogeneous assay without centrifugation or conventional filtration. In general, conventional filtration systems require expensive membranes which are inconvenient and often cannot be reused. Centrifugation is inconvenient to automate, and tubes or wells do not offer adequate surface area or geometry to provide a high binding capacity and rapid binding.

SUMMARY OF THE INVENTION

A method for separating a surface bound component in a binding assay from components dissolved or suspended in a liquid medium is provided wherein a matrix of beads provides the surface for binding and the liquid medium is separated from the beads by aspiration through a tube inserted into the matrix and having an inside cross section sufficiently small to preclude aspiration of or clogging by the beads. Usually the beads will have a number of specific binding pair (sbp) members affixed to their surface which are capable of binding a complementary sbp member that is the analyte, an analog of the analyte or a reagent capable of binding the analyte. The separation will usually involve the removal of a conjugate of a sbp member that is present in the liquid medium from the same conjugate bound to the bead matrix.

One embodiment of the invention is a method for carrying out a separation in a ligand binding assay in which a sbp member and a sample are combined in an aqueous medium under conditions wherein analyte if present in the sample forms a complex with the sbp member. The medium is combined with beads under conditions wherein the beads bind to the sbp member complex. The aqueous medium is then aspirated from the beads by means of a tube inserted into the bead matrix wherein the size of the beads is large enough to permit removal of the liquid medium but small enough to prohibit aspiration of the beads.

In another embodiment of the invention a method for carrying out a separation of a first sbp member from an aqueous medium is described, the improvement being the use of a matrix of beads of a size from 0.2 to 2.5 mm in diameter to which are bound an sbp member capable of binding the first sbp member and an aspiration tube to separate beads having sbp members bound thereto from the medium.

Yet another embodiment of the invention is an assay method for the determination of an analyte in a sample suspected of containing the analyte wherein the analyte is an sbp member and a labeled sbp member is separated from the assay mixture in relation to the concentration of analyte present in the mixture. The method comprises combining in an assay medium the sample, labeled sbp member and beads where the labeled sbp member is capable of binding to the beads; incubating the beads with sufficient amounts of assay medium containing labeled sbp member wherein the volume of assay medium is no greater than that which will cover the beads; aspirating the assay medium from the beads using an aspiration tube having one or more orifices each of a diameter smaller than the minimum diameter of the smallest bead wherein labeled sbp members bound to beads are separated from those not bound; and examining the beads for the presence of the labeled sbp member.

Still another embodiment of the invention is an assay for an analyte in a sample suspected of containing the analyte in which the analyte is an sbp member consisting of a ligand and its complementary receptor wherein the analyte becomes bound to a complementary sbp member in a solution in the presence of beads where the sbp member-analyte complex becomes bound to the surface of the bead matrix. The improvement comprises separating the solution from the complementary sbp member-analyte complex bound to the beads by inserting in the bead matrix an aspiration tube having one or more orifices each of a diameter smaller than the minimum diameter of the smallest bead.

In still another embodiment of the invention, a method for conducting an assay is described which comprises a.) forming in an aqueous medium bound and free species of an analyte; b.) incubating the medium with a matrix of beads capable of binding to either the bound or free species in a volume of medium no greater than that required to cover the bead matrix; c.) aspirating the medium from the beads following an incubation period, where the size of the beads allows separation of the liquid medium free of the beads; and d.) examining the beads for the presence of either the bound or free species.

In yet another embodiment of the invention a method for carrying out a separation in an assay is described which comprises combining in a liquid medium an sbp member and a sample under conditions wherein analyte if present in the sample forms a complex with the sbp member; combining the medium with a matrix of 50 to 50,000 non-porous beads having a size of from 0.2 to 2.5 mm in diameter under conditions wherein the beads bind the sbp member; separating the medium from the beads by aspiration using an aspiration tube having one or more orifices each of a size smaller than the minimum diameter of the smallest bead such that the diameter of the beads is large enough to permit removal of the liquid medium without aspiration of the beads.

In another embodiment of the invention, a method for carrying out a separation in a heterogeneous immunoassay comprises combining an aqueous medium containing a member of an antigen-antibody pair and a sample with a matrix of non-porous beads under conditions wherein the beads can bind to the member of an antigen-antibody pair and separating the aqueous medium from the beads by means of an aspiration tube wherein the minimum diameter of the beads is larger then the orifice of the aspiration tube thereby allowing removal of the aqueous medium while prohibiting aspiration of the beads is described.

In still another embodiment of the invention, a method for carrying out a separation in a binding assay is described. The method comprises combining an aqueous medium containing a first sbp member and a matrix comprised of beads to which is bound a second sbp member which is the same or different from the first member under conditions wherein the first member binds directly or indirectly to the second member; and aspirating the aqueous medium by means of a tube inserted in the bead matrix wherein the size of the beads is large enough to permit removal of the aqueous medium without aspiration of beads.

DETAILED DESCRIPTION OF THE INVENTION

This invention provides a large surface area for binding assays which can be washed as readily as tubes or microtiter plate wells without the need for membranes, filters, magnetic separation, or centrifugation. The method employs a matrix comprised of beads, preferably non-porous, that are of sufficient size so that they will not be aspirated by or clog a tube that is immersed into the bottom of the matrix for the purpose of aspirating liquid surrounding the beads.

Binding assays such as ligand binding assays which include nucleic acid binding assays, currently employ a variety of different types of solid phases. Examples of the types of solid phases used include latex particles, chromium dioxide ferromagnetic particles, magnetic cellulose particles, glass beads, polystyrene balls, glass-fiber filter paper, cellulose filter paper, nitrocellulose membranes, and polystyrene microfilter plates, plastic coated tubes, and the like.

The invention provides a binding assay method which is more convenient and rapid than standard binding assays which employ centrifugation or filtration. The invention has particular application to the assay of an analyte in a sample where a separation step is required.

Before proceeding further with the description of the specific embodiments of the present invention, a number of terms will be defined.

"Analyte" means the compound or composition to be measured, the sample or material of interest. The analyte can be a member of a specific binding pair (sbp) and may be a nucleic acid or oligonucleotide or may be a ligand, which is mono- or polyvalent, usually antigenic or haptenic, and is a single compound or plurality of compounds which share at least one common epitopic or determinant site. The analyte can also be a component of a particle or can become bound to a particle during an assay. Exemplary of an analyte that is a component of a particle is an antigen on the surface of a cell such as a blood group antigen (A, B, AB, O, D, etc.) or an HLA antigen. The binding involved when an analyte becomes bound to a particle can be specific or non-specific, immunological or non-immunological.

The polyvalent ligand analytes will normally be poly(amino acids), i.e., polypeptides and proteins, polysaccharides, nucleic acids, and combinations thereof. Such combinations include components of bacteria, viruses, chromosomes, genes, mitochondria, nuclei, cell membranes and the like.

For the most part, the polyepitopic ligand analytes employed in the subject invention will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

A wide variety of proteins may be considered as to the family of proteins having similar structural features, proteins having particular biological functions, proteins related to specific microorganisms, particularly disease causing microorganisms, etc.

The monoepitopic ligand analytes will generally be from about 100 to 2,000 molecular weight, more usually from 125 to 1,000 molecular weight. The analytes of interest include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which include cocaine and benzoyl ecgonine, their derivatives and metabolites, ergot alkaloids, which include the diethylamide of lysergic acid; steroid alkaloids; iminazoyl alkaloids; quinazoline alkaloids, isoquinoline alkaloids; quinoline alkaloids, which include quinine and quinidine; diterpene alkaloids, their derivatives and metabolites.

The next group of drugs includes steroids, which includes the estrogens, androgens, androcortical steroids, bile acids, cardiotonic glycosides and aglycones, which includes digoxin and digoxigenin, saponins and sapogenins, their derivatives and metabolites. Also included are the steroid mimetic substances, such as diethylstilbestrol.

The next group of drugs is lactams having from 5 to 6 annular members, which include the barbituates, e.g. phenobarbital and secobarbital, diphenylhydantonin, primidone, ethosuximide, and their metabolites.

The next group of drugs is aminoalkylbenzenes, with alkyl of from 2 to 3 carbon atoms, which includes the amphetamines, catecholamines, which includes ephedrine, L-dopa, epinephrine, narceine, papaverine, and their metabolites.

The next group of drugs is benzheterocyclics which include oxazepam, chlorpromazine, tegretol, imipramine, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs includes the vitamins such as A, B, e.g. $B_{12}$, C, D, E and K, folic acid, thiamine.

The next group of drugs is prostaglandins, which differ by the degree and sites of hydroxylation and unsaturation.

The next group of drugs is antibiotics, which include penicillin, chloromycetin, actinomycetin, tetracycline, terramycin, the metabolites and derivatives.

The next group of drugs is the nucleosides and nucleotides, which include ATP, NAD, FMN, adenosine, guanosine, thymidine, and cytidine with their appropriate sugar and phosphate substituents.

The next group of drugs is miscellaneous individual drugs which include methadone, meprobamate, serotonin, meperidine, amitriptyline, nortriptyline, lidocaine, procaineamide, acetylprocaineamide, propranolol, griseofulvin, valproic acid, butyrophenones, antihistamines, anticholinergic drugs, such as atropine, their metabolites and derivatives.

Metabolites related to diseased states include spermine, galactose, phenylpyruvic acid, and porphyrin Type 1.

The next group of drugs is aminoglycosides, such as gentamicin, kanamicin, tobramycin, and amikacin.

Among pesticides of interest are polyhalogenated biphenyls, phosphate esters, thiophosphates, carbamates, polyhalogenated sulfenamides, their metabolites and derivatives.

For receptor analytes, the molecular weights will generally range from 10,000 to $2 \times 10^8$, more usually from 10,000 to $10^6$. For immunoglobulins IgA, IgG, IgE and IgM, the molecular weights will generally vary from about 160,000 to about $10^6$. Enzymes will normally range from about 10,000 to 1,000,000 in molecular weight. Natural receptors vary widely, generally being at least about 25,000 molecular weight and may be $10^6$ or higher molecular weight, including such materials as avidin, DNA, RNA, thyroxine binding globulin, thyroxine binding prealbumin, transcortin, etc.

Member of a specific binding pair ("sbp member") means one of two different molecules, having an area on the surface or in a cavity which specifically binds to and is thereby defined as complementary with a particular spatial and polar organization of the other molecule. The members of the specific binding pair are referred to as ligand and receptor (antiligand). These will usually be members of an immunological pair such as antigen-antibody, although other specific binding pairs such as biotin-avidin, hormones-hormone receptors, nucleic acid duplexes, IgG-protein A, DNA-DNA, DNA-RNA, and the like are not immunological pairs but are included in the invention.

"Ligand" means any organic compound for which a receptor naturally exists or can be prepared.

"Receptor" means any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, protein A, complement component Clq, and the like.

"Beads" shall mean non-porous and porous particles, with non-porous particles being preferred. The beads may be of any convenient material to which a sbp member can be non-diffusively bound and which does not dissolve in or react adversely with the ligand medium. Usually beads will be plastic such as polystyrene, polyacrylate, polyacetate, polyvinylchlorite, polyurethane teflon and the like or they may be metallic such as steel, nickel, copper and preferably will be ceramic including, for example, quartz, glass, and the like. The primary requirement being that they have a specific gravity sufficient such that they will sink when immersed in the liquid assay medium and will therefore form a bed of beads or a matrix at the bottom of the vessel containing the liquid. The beads will usually be of a defined approximately uniform, size, preferably 0.2 to 2.5 mm, and will have either a rough or smooth surface, preferably smooth. Preferably the beads are rounded or oblong, usually approximately spherical and have surface properties which minimize non-specific binding. As used in the binding assays of the invention, the beads will usually be polyfunctional and will have bound to, or be capable of specific non-covalent binding to, an sbp member, such as an antibody, avidin, biotin, lectins, protein A, and the like.

"Label" means a member of the signal producing system that is conjugated to an sbp member. The label can be isotopic or non-isotopic, usually non-isotopic, including catalysts such as an enzyme, a chromogen such as a fluorescer, dye or chemiluminescer, a radioactive substance, a particle, and so forth.

"Signal producing system" means a signal producing system having one or more components, at least one component being a label. The signal producing system generates a signal that relates to the presence or amount of analyte in a sample. The signal producing system includes all of the reagents required to produce a measurable signal. The label will usually be conjugated directly or indirectly to an sbp member that may be an analog of the analyte or a binding surrogate of the analyte or conjugated to an sbp member capable of binding directly or indirectly to the analyte or analyte analog. Components of the signal producing system may be radioactive substances, coenzymes, substances that react with enzymic products, enzymes, and catalysts, solid particles, fluorophors, chromophors, latex particles and the like. The signal producing system provides a signal detectable by external means, preferably by measurement of the degree of aggregation of particles or by use of electromagnetic radiation, desirably by visual examination. For the most part, the signal producing system will involve a chromophoric substrate and enzyme, where chromophoric substrates are enzymatically converted to dyes which absorb light in the ultraviolet or visible region, phosphors, fluorescers or chemiluminescers, radioactive atoms, electroactive groups and the like.

The signal-producing system can include at least one catalyst, usually an enzyme, and at least one substrate and may include two or more catalysts and a plurality of substrates, and may include a combination of enzymes, where the substrate of one enzyme is the product of the other enzyme. The operation of the signal producing system is to produce a product which provides a detectable signal related to the amount of analyte in the sample.

Of particular interest are enzymes which involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme which employs the hydrogen peroxide to oxidize a dye precursor, that is, a peroxidase such as horseradish peroxidase, lactoperoxidase, or microperoxidase. Of particular interest in the subject invention is the use of a horseradish peroxidase enzyme system.

"Non-specific binding" means non-covalent binding of a label or molecule to a surface that is relatively independent of specific surface structures. Such non-specific binding will usually result from charge or electrostatic interactions between oppositely charged particles or between particles having the same charge where a polyionic reagent having a charge opposite thereto is employed. Non-specific binding may also result from hydrophobic interactions, hydrogen bonding, Van der Waals forces, and the like.

"Ancillary materials" means various additional materials employed in an assay in accordance with the present invention. For example, buffers will normally be present in the assay medium, as well as stabilizers for the assay medium and the assay components. Frequently, in addition to these additives, additional proteins may be included, such as albumins, or surfactants, particularly non-ionic surfactants, binding enhancers, e.g., polyalkylene glycols, or the like.

As mentioned above, one aspect of the present invention involves a method for separating a sbp-label conjugate from a liquid medium. The method comprises combining a liquid medium containing the conjugate with beads to which are bound an sbp member capable of direct or indirect binding to the conjugate under conditions for binding the conjugate to the beads. Preferably, for achieving complete separations the liquid medium containing the conjugate is of a volume that is not significantly in excess of that needed to completely cover the matrix of beads and may be insufficient to cover the beads and the amount of sbp member bound to the beads will be at least sufficient to bind all the conjugate. Included within the invention, however, is a separation method wherein the volume of liquid is substantially greater than the volume required to cover the beads. In either instance, the method for conducting the separation remains the same. After incubation the liquid medium is first incubated with the matrix, which will usually be carried out in a vessel that is not otherwise equipped with a filtration device and is therefore impermeable to the liquid. The medium is then separated from the beads by means of aspiration. The aspiration is carried out using an aspiration tube having one or more orifices preferably one orifice, having, when the tube has a circular cross section, a diameter smaller than the diameter of the smallest bead with which it comes in contact. When the tube cross section is not circular at least the shortest or the longest cross sectional diameter of the orifice must be smaller than the corresponding bead diameter. As a result the liquid is efficiently separated from the matrix without loss of beads.

In carrying out the invention, a liquid, usually aqueous, medium will be employed. Other polar solvents may also be employed, usually oxygenated organic solvents from one to six, more usually from one to four, carbon atoms, including alcohols, ethers, and the like. Usually these cosolvents will be present in less than about 40 weight percent, more usually in less than about 20 weight percent. Generally, a pH range of 5 to 10, more usually 6 to 9, will be used. Another consideration with respect to the pH of the assay is the maintenance a significant level of binding of sbp members while optimizing signal producing proficiency. In some instances, a compromise will be made between these considerations. Various buffers may be used to achieve the desired pH and maintain the pH during the determination. Illustrative buffers include borate, phosphate, carbonate, Tris, barbital, and the like. The particular buffer employed is not critical to this invention; however, in individual separations or individual assays, one buffer may be preferred over another.

Moderate temperatures are normally employed for carrying out the separation and assay and usually constant temperatures during the period for conducting the method. The temperature for the assay, particularly involving an immunoassay, will generally range from about 0° to 50° C., more usually from about 15° to 40° C.

While the concentrations of the various reagents will generally be determined by the concentration range of the sbp member in the liquid medium or of the analyte in an assay, the final concentration of each of the reagents will normally be determined empirically to optimize the sensitivity and specificity of the separation or of the assay over the range of interest.

In a binding assay, the aqueous medium can also contain one or more members of a signal producing system. The concentration of the various members of the signal producing system will vary and be dependent upon the concentration range of interest of the analyte and the type of measurement or assay involved. As a general point, the concentration of the various members of the signal producing system will be selected to optimize the signal produced in relation to the concentration range of interest of the analyte.

The present invention has application to assays for an analyte in a sample suspected of containing the analyte. The analyte is an spb member. In one example of the assay the sample is combined in a liquid, usually aqueous, medium comprised of a first spb member complementary to the analyte which may be dispersed in the medium or bound to the surface of beads comprising a matrix of 50 to 50,000, preferably 200 to 2000 beads. The beads are simultaneously or subsequently contacted with a second spb member bound to a label. The label is at least a part of a signal producing system for producing a detectable signal in relation to the amount of analyte in the sample. After incubation to permit the second sbp member to bind to the beads, unbound second sbp member is removed by aspiration of the medium, the beads are then combined with any remaining members of the signal producing system and the amount or presence of analyte is determined in relation to the signal.

In one preferred practice of the invention, a sample suspected of containing an analyte which is an sbp member is combined in a liquid medium with a complementary sbp member and a labeled sbp member when the complementary sbp member is not bound to a label. The medium is simultaneously or thereafter contacted with a matrix of beads having bound thereto sufficient amount of an sbp member to completely bind directly or indirectly all of a complementary sbp member present in the medium at a volume to just cover or insufficiently cover the matrix surface thereby ensuring contact for binding between the bead and the labeled sbp member. Following incubation of the medium with the beads, the medium is removed by aspiration. After addition of any remaining members of the signal producing system the beads containing bound label are examined for the presence of a detectable signal as an indicator of the presence or amount of the analyte.

In a particularly preferred embodiment of the invention, a sample suspected of containing an analyte which is an sbp member, usually an antigen, is combined in an aqueous medium with a complementary sbp member, usually an antibody, which is bound to or capable of binding to the surface of beads. A second sbp member that is capable of binding to the complementary sbp member as a function of the presence of the analyte and is bound to or capable of binding to a label is also combined in the aqueous medium. The medium is then combined with the label and a matrix of beads if these components are not already present, and the mixture is incubated to permit binding of the label to the beads. An aspiration tube designed to prevent aspiration of the beads is then inserted into the matrix and the aqueous medium is separated from the beads by aspiration. Optionally, a wash solution can then be added and removed by aspiration. Due to the density and size of the beads, the beads are easily suspended by a jet of wash solution and then settle quickly so as to enable efficient aspiration of the wash solution from the beads.

The presence or amount of label on the bead matrix is then determined in relation to the amount of label retained on the matrix when using a sample known to contain the analyte or a specific amount of the analyte.

As a matter of convenience, the reagents for conducting an assay can be provided in a kit in package combination in predetermined amounts for use in assaying for an analyte. The kit comprises (a) an sbp member complementary to the analyte, (b) a matrix of beads capable of binding specifically to the analyte or a receptor for the analyte wherein the beads have an average diameter of 0.2 to 2.5 mm, and (c) a label bound to or capable of binding to the analyte or receptor for the analyte. The kit can also include other reagents for generating a signal in relation to the amount of analyte in the sample. Additionally, the kit can further comprise a releasing agent for reversing the binding between the particles. Ancillary agents can be included as necessary.

In the invention described herein, the beads are usually non-porous, usually glass or latex and normally are between 0.2 and 2.5 mm average diameter. Most preferably, the beads are from 0.5 to 2 mm average diameter. The beads are usually approximately spherical and may have a rough or smooth surface.

To be of value in a binding assay, the beads must have specific surface properties. The surface must have low non-specific binding to the label and sbp members while providing an efficient means of separation of label that is bound to analyte or its complementary sbp member from label that is unbound. The size and shape of the beads is selected to maximize the ratio of bead surface to the volume of the liquid medium while permitting easy penetration of the aspiration tube into the bead matrix and efficient separation of the liquid medium from the matrix. A higher surface to volume ratio permits more rapid binding of the label to the beads but necessitates use of smaller beads that can interfere with efficient separation. Normally beads ranging in size from 0.2 to 2.5 mm have been found to be most useful. In addition it will frequently be desirable to maximize the surface density of sbp members on the beads in order to maximize their binding capacity. In general surface densities should be least one sbp member molecule per 10,000 $nm^2$, preferably at least one per 1000 $nm^2$, most preferable at least one per 100 $nm^2$ and will preferably be of sufficiently high density to bind all the complementary sbp member present in the assay medium that contacts the beads.

Because of the high surface area of beads, attention must be paid to the surface properties so that background nonspecific binding remains low. Where avidin is used as the sbp member bound to the beads, nonspecific binding can be reduced by drying the glass particles in the presence of sucrose after the binding of avidin to the beads. Examples of coatings in addition to sugars, which have been found useful include bovine serum albumin (BSA), poly(vinyl alcohol), casein and non-fat milk.

The aspiration tube used to aspirate liquid away from the beads will have one or more, usually one, orifice. The orifice, which may be circular, oblong, rectangular or other convenient shape, is shaped so as to prevent clogging of the tube by the beads during aspiration. Preferably, the tube will have a 0.5–3 mm outside diameter to permit easy penetration into the matrix and when cylindrical, will conveniently have a bore diameter of from 0.1 to 1.0 mm, more usually 0.2 to 0.5 mm. The size of the tube orifice will always be such that the beads, no matter what the shape, cannot be aspirated into the tube. Prevention of aspiration of the beads is preferably obtained by having the tube orifice smaller than the beads. Alternatively, the orifice may be larger than the bead diameter but covered by a porous frit, membrane or screen which prohibits aspiration of the beads into the tube. The tube may be made of any convenient material with sufficient rigidity to permit penetration into the matrix as for example, steel, polypropylene, nylon, titanium and the like and will usually have surfaces that are easily washed free of proteins, particularly relatively smooth surfaces that are not abraded by the beads.

The beads are treated so as to have an sbp member bound to their surface which member will specifically bind, directly or indirectly, to the analyte or an sbp member complementary to the analyte. In a preferred practice of the invention, the beads have bound to them a ligand or receptor that will permit the beads to be used for a variety of different assays. For example, avidin can be covalently bound to spherical glass beads of 0.5 to 1.5 mm. A matrix of these beads is mixed in an aqueous medium with biotin-labeled antibodies to an analyte, a sample containing the analyte, and a labeled antibody or ligand that will bind to the biotin-labeled antibodies as a function of the amount of analyte in the solution. Because the beads bind to biotin and biotin can be bound to any antibody, the same beads can be used for most antibody-antigen pairs. After sufficient incubation to permit binding of the labeled antibody or ligand to the biotinylated antibody and binding of the latter to the beads, the solution is removed from the beads by aspiration with the above described tube. Wash solution is then added by means of the same or a different tube and liquid again aspirated. After repeating the washing cycle, the label is detected and the amount of label is related to the amount of analyte in the sample.

Use of the method of the invention is applicable to any heterogeneous binding assay for the analyte defined above. Specific assays include for example, assays for digoxin, triiodothyronine (T3), thyroid stimulating hormone (TSH), thyroid binding globulin (TBG), vitamin B12, hepatitis antigens (e.g. $HB_sAg$) and hepatitis antibodies, the human immunodeficiency virus (HIV) related antigens and antibodies. In each system, biotinylated antibody or antigen that is complementary to the analyte is used. Sbp members other than avidin may be attached to the beads, such as, haptens, antibodies, antigens, nucleic acid binding proteins, oligonucleotides, receptors such as protein A and the like, whereupon the complementary sbp member conjugated to the antibody or antigen complementary to the analyte is used.

In these assays any convenient label can be used, frequently an enzyme, preferrably alkaline phosphatase or a peroxidase such as horseradish peroxidase (HRP). In assays for small molecules, the label can be conjugated directly to an analog of the analyte. Thus in assays for digoxin and T3, these compounds are covalently bound to HRP to provide a label-sbp member conjugate.

In the assay for TSH, an antibody conjugated to HRP can be used together with a second non-competing biotinylated antibody that can bind to TSH and become bound to the beads. After incubation for 30 to 60 minutes of the beads with both antibodies and the sample, the solution is removed, the beads washed four times, and then incubated with tetramethylbenzidine and hydrogen peroxide solution. Color develops in the solution within 15 minutes and can be read spectrophotometrically after aspirating the solution from the beads or by dilution of the solution-bead mixture and allowing the beads to settle so that the absorbance of the solution covering the beads can be read directly.

In one variant of the heterogeneous ligand assays described above, a hapten such as fluorescein can be substituted for the HRP bound to an sbp member. In such a system, anti-TSH-fluorescein, digoxin-fluorescein and T3-fluorescein conjugates can be used in place of the enzyme conjugates. An HRP-labeled antifluorescein conjugate is then included in the assay medium or added to the beads after incubation of the beads with the assay medium. An advantage of such a system is that a single enzyme reagent can be used for all assays. This eliminates the need to prepare enzyme conjugates with a different antibody for each assay, a procedure which is often problematic due to instability and potential non-specific binding of different enzyme conjugates. By contrast, binding of fluorescein to different antibodies is a relatively simple and reproducible process.

In another preferred embodiment of the invention all assays use the same two generic reagents, non-porous beads bound to a generic receptor such as avidin and an enzyme bound to a second generic receptor such as anti-fluorescein. In each of these assays two additional sbp members are used, one conjugated to biotin and one conjugated to fluorescein. In such an assay the biotin and fluorescein bound sbp members are allowed to bind with each other or with the analyte in the solution phase prior to combining with the bead matrix wherein the binding reaction proceeds more rapidly then when binding of analyte occurs at a surface as normally occurs in an enzyme linked immunosorbent assay (ELISA).

In an assay for a multiepitopic analyte such as TSH specific TSH, antibodies are conjugated to biotin for later capture by avidin coated glass beads of the invention. The second TSH specific antibody is conjugated to fluorescein. The enzyme conjugate has at least one HRP linked to an anti-fluorescein antibody. After a short incubation of a mixture of all of the components, glass beads coated with avidin are added to bind the complex (biotin-antibody:TSH:antibody-fluorescein:anti-fluorescein-HRP) to the surface.

A matrix containing a sufficient amount of beads is added such that the entire antibody-sample incubation volume is completely entrapped within the spaces between the beads. This maximizes the surface to volume ratio and provides for relatively short diffusion distances and thereby permits quantitative binding of the biotinylated antibody without shaking.

The surface of the beads is then washed by plunging an aspiration tube to the bottom of the matrix of beads and successively adding and aspirating wash solution. Due to the density and size of the beads, the beads can be easily suspended by the jet of wash solution and then settle quickly. The beads are large enough that they are not aspirated by the wash probe. Substrate is then added in sufficient volume to cover the beads completely and the amount of enzyme product is determined photometrically after a suitable incubation time and compared to the amount of product provided using a sample of known concentration of analyte.

The chemistry and methodology of the invention in certain preferred embodiments have the following significant advantages over the standard ELISA chemistry: 1) avidin coated glass beads are generic to all assays; 2) analyte to antibody binding in solution phase results in very rapid kinetics compared to those achieved with antibody immobilized on a solid surface; 3) presence of a large solid surface area with high antibody binding capacity results in rapid kinetics of capture; and 4) the capture surface need not be added quantitatively.

In addition, the anti-fluorescein-HRP conjugate is generic to all assays and will be the only enzyme reagent to optimize and stablize. This is in contrast to the standard ELISA formats where separate enzyme reagents are required for each assay. The chemistry to link biotin or fluorescein to antibodies or haptens is simple and efficient. (See, for example, D. M. Boorsma, *Immunocytochemistry* 2:155 (1983)). The stability of the biotin or fluorescein conjugates will be as good as the antibodies used in the conjugate.

EXAMPLES

The examples which follow are illustrative and not limiting of the invention. Unless otherwise indicated, reagents were obtained from commercial sources and, where applicable, were used according to manufacturer's directions.

The following abbreviations are used throughout the examples:

| | |
|---|---|
| Ab$_{Dig}$ | antidigoxin antibody |
| Ab$_F$ | anti-fluorescein antibody |
| Ab$_{T3}$ | anti-triiodothyronine antibody |
| ANS | 8-Anilinonaphthalene-1-sulfonic acid |
| Biotin-LC—NHS | succinimidyl 6-(biotinamido) hexanoate |
| Bis-NH$_2$ | 2,2'-Oxybis(ethylamine) |
| BSA | Bovine serum albumin |
| DCC | N,N'-Dicyclohexylcarbodiimide |
| Dig | Digoxin |
| Dig-CMO | Digoxin carboxymethyl oxime |
| Dig-LC—F | digoxin carboxymethyl oxime-LC—NH-carboxyfluorescein |
| F | Fluorescein |
| EDAC | 1-ethyl3(3-Dimethylaminopropyl)carboiimide |
| EDTA | ethylenediaminetetraacetic acid, tetrasodium salt |
| F | Fluorescein |
| F—COOH | 6-Carboxyfluorescein |
| F—LC—NH$_2$ | carboxyfluorescein-LC—NH$_2$ |
| GB | Glass beads |
| HRP | Horseradish peroxidase |
| LC | 3,3'-diamino-N-methyldipropylamine |
| NaPi | Sodium phosphate buffer |
| NHS | N-Hydroxysuccinimide |
| o/n | overnight |
| PBS | Phosphate-buffered saline |
| Sulfo-NHS | Sulfo-N-hydroxysuccinimide |
| T$_3$ | 3,3',5-triiodo-L-thyronine |
| TMB | 3,3',5,5'-tetramethylbenzidine-2 HCl |
| TNBSA | 2,4,6-Trinitrobenzesulfonic acid |

Example 1: Heterogeneous enzyme-based immunoassay for detection of digoxin

Preparation of Materials

A. Preparation of HRP-succinyl-oxybis (ethylamide)-digoxin

1. Preparation of HRP-succinyl-bis-NH$_2$. The reagent was prepared in two successive steps: 1.) the two reactive amino groups of the native HRP were converted into carboxyl groups by succinylation to HRP-COOH; 2.) the HRP-COOH was then reacted with an excess amount of oxybis(ethylamine) and EDAC to generate HRP-succinyl-bis-NH$_2$.

Succinylation of HRP. Into 2 mL solution of 20mg/mL HRP in 0.1M Borax at room temperature, 40 µL of 2.5M succinic anhydride in DMF was added. After stirring for 20', another 40 µL of succinic anhydride solution was added and the mixture incubated for one more hour at room temperature. The small molecular weight materials were removed by purifying the reaction mixture on a Sephadex G-25 column, equilibrated in 0.005M sodium phosphate buffer (NaPi)/pH=7.0. The HRP-COOH was concentrated to 20mg/mL HRP-COOH using Amicon YM-10 membrane. The reaction was followed by gel electrophoresis and TNBSA titration of reactive amino groups.

Introduction of reactive amino groups into the succinylated HRP.

To 1 mL of 20 mg/mL of HRP-COOH in 0.005M NaPi/pH=7.0, 8.86 mg of solid 2,2'-oxybis(ethylamine) dihydrochloride was added. The pH of the reaction mixture was readjusted to 7.0 using 0.2M Na$_2$HPO$_4$. Into this mixture 14 mg EDAC was added and the reaction mixture incubated at 4° C. for 2 hours with gentle stirring. The unreacted small molecular weight materials were removed from the HRP-succinyl-bis-NH$_2$ by a Sephadex G-25 column, equilibrated in 0.05M NaPi, 0.05M NaCl/pH=7.8. The number of reactive amino groups was determined by TNBSA to be 1.51 per HRP-succinyl-bis-NH$_2$. The HRP-succinyl-bis-NH$_2$ was purified on CM-Sephadex (C-50) and two main products were separated: (1) HRP-succinyl-bis-NH$_2$ with one amino group and (2) HRP-succinyl-bis-NH$_2$ with two amino groups per HRP.

2. Preparation of Digoxin-NHS. A solution, containing 20 mg of Dig-CMO, 5 mg of NHS, and 9 mg of EDAC in 0.2 mL of DMF, was incubated at room temperature by stirring overnight (o/n). After removing the unsoluble materials by filtration, the solvent (DMF) was removed by rotary evaporation. The product was stored desiccated at 4° C.

3. HRP-Succinyl-Oxybis(ethylamide)-Digoxin. To 4 mL of 1.3 mg/mL HRP-succinyl-bis-NH$_2$ (with two reactive amino groups per HRP) in 0.05M NaPi, 0.05 NaCl/pH=7.8 at 4° C., 1.3 mL of 1 µmole/mL Dig-NHS in DMF was added (4×324 µL; 325 µL of Dig-NHS solution was added after each 15 minutes). The reaction mixture was then incubated for three hours by stirring at 4° C. The reaction was stopped by adding 150 µL of 2M glycine/pH=8.0 and incubating for an additional one hour at room temperature. Finally, the reaction mixture was centrifuged to remove the unsoluble substances and purified on Sephadex G-25 in 0.05M Borax. The hapten number was estimated to be about 2 by titrating the remaining reactive amino groups using TNBSA. The conjugate was stored at 4° C.

B. Preparation of Ab$_{Dig}$-Biotin

Anti-digoxin antibodies were purified by immobilized Protein A to obtain the Ab IgG fraction. Then the Ab$_{Dig}$-biotin was prepared by mixing the Ab (about 2–2.5 mg/mL in 0.05M NaPi, 0.05M NaCl/pH 7.8) and Biotin-LC-NHS (first solubilized in DMF and a small aliquot used for the reaction) and incubating for three hours at 4° C. In the reaction mixture, the molar ratio of the reactants was Ab:Biotin-LC-NHS=1:25. The uncoupled biotin was removed by Sephadex G-25 column. The final conjugate was stored in 0.05M NaPi, 0.001% Thimerosal/pH=7.4 at 4° C. or frozen.

C. Preparation of Dig-LC-F

This reagent was prepared in three successive steps by preparing (1) F-NHS, (2) F-LC-NH$_2$, and (3) Dig-LC-F.

1. Preparation of F-NHS. To the 2 mL of 100 mg/mL 6-carboxyfluorescein and 30.6 mg/mL of NHS in DMF was added, 0.4 mL of 275 mg/mL of DCC. The mixture was stirred o/n at room temperature in the dark. The formed dicyclohexylurea was removed by filtration. The formation of F-NHS was checked by thin layer chromatography TLC on silica plates, using CH$_2$CH$_2$:methanol:acetic acid=85:15:1 solvent system. DMF was removed by rotary evaporation, and the product (F-NHS) was dried further under strong reduced pressure and stored desiccated at 4° C.

2. Preparation of F-LC-NH$_2$. To the 1.5 mL of LC, 1.2 mL of 125 mg/mL F-NHS in DMF was added and incubated at room temperature o/n, by stirring in the dark. The molar ratio of F-NHS:LC=1:40. The reaction mixture was diluted 1/20 with 0.5M NaPi/pH 5.0, the pH of the mixture was adjusted to 5.0 by phosphoric acid. The whole mixture was loaded onto a (2.5×10 cm) of BioRex-70 column, equilibrated in 0.5M NaPi/pH=5.0. After loading, the column was washed with the starting buffer until all of the 3,3'-diamino-N-methyldipropylamine was removed (monitored with TNBSA reaction). The column was washed with 0.001M NaPi/pH=6.0 to remove the 6-carboxyfluorescein contaminant. Washing with low ionic strength buffer removes not only the 6-carboxyfluorescein but also fluorescein containing contaminants. The column was washed with dionized water (D-H$_2$O) to remove the salts. Finally, the column was stripped by 0.8M NH$_4$OH. The ammonium hydroxide was removed by lyophilization. After checking the purity, the product was stored desiccated at −20° C. The reaction was followed (and the purity of the product was checked) by paper electrophoresis (0.05M NaPi/pH=5.8, 20 minutes and by TLC (C$_{18}$ plates, using 50% methanol in D-H$_2$O as solvent).

3. Preparation of Dig-LC-F. A solution, containing 23.05 mg (0.05 mmoles) of Dig-CMO, 50.35 mg (0.1 mmoles) fluorescein-LC-NH$_2$ and 19.2 mg (0.1 mmoles) EDAC in 1.5 mL of DMF/DMSO (5:1) solvent was stirred overnight at room temperature in the dark. The Dig-LC-F and Dig-CMO were precipitated out by adding 3 mL of D-H$_2$O, filtered, and the solvent discarded. The filtered material was resolubilized in a solvent system consisting of CH$_2$CH$_2$:methanol:acetic acid=60:40:5 and was loaded onto a (1.5×20 cm) silica gel column in the same solvent system. Under these conditions, Dig-CMO moved ahead of Dig-LC-F conjugate, and the F-LC-NH$_2$ remained bound to the top of the column. The purity of the material was checked by TLC silica gel plates, using the solvent system described above, and by electrophoresis on paper at pH=5.8. The solvents were removed from the purified material by rotoevaporation under reduced pressure, the product was resolubilized into a minimum volume of methanol/DMF (70:30) and centrifuged to remove any unsoluble materials (silica gel). The last step was performed to remove most of the silica gel, which may be solubilized and co-eluted with the product during the purification. The product was stored in methanol/DMF (70:30) solvent system at −10° C. to −20° C. The concentration of the product was determined by A$_{490}$ from a standard curve constructed using known amounts of 6-carboxyfluorescein.

D. Preparation of Anti-Fluorescein-HRP Conjugate

The anti-fluorescein antibodies used were monoclonal anti-fluorescein antibodies prepared using standard monoclonal antibody techniques (Milstein, C. and Kohler, G., *Nature* 256:495 (1975)). Before conjugation to HRP, these antibodies were purified to IgG fraction by immobilized Protein A or by Ab$_x$ matrix (combined with a sizing column of Sephacryl S-200). The working pH range for the latter was 5.8–7.0.

1. Preparation of HRP-NHS. Succinylated HRP (HRP-COOH) was used for the preparation of the conjugate. To the 1.25 mL of 20 mg/mL HRP-COOH in 0.003M NaPi/pH=6.9, 13 mg of sulfo-NHS was added. After adjusting the pH of the mixture back to 6.9 by 0.2M Na$_2$HPO$_4$, 20 mg EDAC was added. The reaction mixture was incubated for 20 minutes at room temperature and then purified on a Sephadex G-25 column in PBS/pH=7.1. The purified HRP-NHS was immediately used for conjugation with fluorescein antibody (Ab$_F$).

2. Preparation of anti-fluorescein-HRP conjugate (Ab$_F$-HRP).

Before conjugating, the fluorescein antibody was dialyzed against 0.02M NaPi, 0.14M NaCl/pH=7.2, and then F$_{520}$ was added to a final concentration equal to that of the binding sites. (F$_{520}$ was used to block the binding sites of the anti-fluorescein antibody.

To 0.9 mL of 20 mg/mL HRP-NHS was added 3 mL of 2 mg/mL Ab $_{F520}$ in PBS/pH7.2 and the mixture incubated at 4° C. for 4.5 hours (if the mixture is concentrated in the beginning, the efficiency of the conjugation chemistry will improve, but care should be taken to minimize the aggregate formation). The reaction was stopped by adding hydroxyl amine to a final concentration of 0.1M in reaction mixture (pH=7.0) and incubated overnight at 4° C. The reaction mixture was concentrated to approximately 2 mL using an Amicon concentrating device with YM-10 membrane, then purified on a Sephacryl S-300 column (1.5×114 cm). The peak material corresponding to MW=200K−250K was used in the assays.

E. Preparation of Avidin-Glass Beads (GB)

Glass beads of approximately 0.75 mm in diameter (Glen Mills, Inc., Maywood, N.J.) were first cleaned by boiling in 5% nitric acid for one hour and then washed with deionized water until the wash was neutral in pH. The beads were dried at room temperature under vacuum.

To 1 kg of the acid-washed beads was added 1 mL of aminopropyltriethoxysilane in 300 mL ethyl acetate. The mixture was then placed on a rotary aspirator, and upon removal of the solvent, the beads were coated with a thin film of the aminosilane reagent. The beads were then transferred to a stainless reactor and heated in an oven at 130° C. overnight under nitrogen/argon atmosphere. After cooling, the beads were used directly in the next step.

To 500 g of the aminated beads in a canted tissue culture flask was added 170 mL 0.1M of sodium borate pH 9.0 for 10 minutes. A solution of succinic anhydride (2.0 g in 20 mL DMF) was added by pipette. The flask was capped and shaken manually. All liquid was removed upon the final addition of succinic anhydride solution, and the beads were washed with deionized water 200 mL×4.

After flushing once with 150 mL 0.1M MES (2-[N-morpholino]ethanesulfonic acid), pH 5.2, the beads were resuspended in MES to the liquid volume to just cover the beads. One hundred milligrams (100 mg) of EDAC (1-ethyl-3-[3-dimethylaminopropyl]carbodiimide) in 2 mL MES was added in one portion and mixed for 5 minutes with manual shaking. Upon removal of the liquid by use of an aspirator, a 20 mL MES solution of avidin (20 mg) and BSA (40 mg) was added in one portion. The beads were mixed manually and more MES buffer was added to just cover the beads. Finally, the culture flask with its contents was placed on an orbital shaker overnight at 4° C.

Further preparation of the beads includes washing the beads with 1N NaCl (200 mL×4) followed by deionized water (200 mL×4). Before and after each wash, the liquid is removed entirely. The beads are then treated with a phosphate-saline buffer (20 mM phosphate, 140 mM NaCl 0.02% NAN$_3$, pH 7.4) containing 0.1% BSA and 2.5% sucrose (150 mL×3). Excess liquid is removed and the wet beads are transferred to a container in a vacuum dessicator.

Finally, after passage through a number 16 or 20 USA Standard Testing Sieve, the beads were dusted with casein powder to prevent sticking together upon storage.

Binding study with $^3$H-biotin indicated that the beads thus prepared incorporated 2–11 μg active avidin/g beads.

F. TMB/H$_2$O$_2$ HRP Substrate

Concentrated stock solutions of TMB and urea hydrogen peroxide were prepared separately and stored frozen. Fresh working substrate solution was prepared each time by diluting and mixing the two reagents together. The concentrated stock solutions were prepared as follows:

TMB stock solution (Solution 1)
  6.82 g Citric Acid (MW=192.1)
  0.652 g TMB×2HCl (MW=313.3)
  Dissolve in 100 mL of D-H$_2$O.
Urea hydrogen peroxide stock solution (Solution 2)
  5 g Na$_3$ Citrate×2 H$_2$O (MW=294.1)
  0.372 g EDTA (Na$_4$) (MW=380.2)
  0.752 g Urea H$_2$O$_2$ (MW=94.07)
  Dissolve in 100 mL of D-H$_2$O.
Preparation of the substrate working solution
  8 mL of 0.125M NaH$_2$PO$_4$
  1 mL of Solution 1
  1 mL of Solution 2
  After mixing, it was used immediately.

Assay Protocol

The protocol of the digoxin assay consists of three parts: 1.) the binding reaction between assay components (biotin-Ab$_{Dig}$+Dig-LC-F+Ab$_F$-HRP) in solution phase to form the complex (biotin-Ab$_{Dig}$-Dig-LC-F-Ab$_F$-HRP); 2.) the binding and separation of the complex from the unbound assay components by GB-Avidin; and 3.) addition of enzyme substrate and color generation.

The digoxin assay was performed in 10×75 mm disposable glass tubes by the sequential addition of 50 μl of the standard in normal human pooled serum or the unknown sample, 50 μl of 1.74 ng/ml Dig-LC-F in assay buffer (0.2M NaPi, 0.14M NaCl and 0.1% BSA to pH 7.4) and 100 μl of a mixture of 80 ng/ml biotin-Ab$_{Dig}$ and 1 μg/ml Ab$_F$-HRP conjugate. The assay mixtures were agitated in a vortex mixer and incubated at 37° C. for 10 minutes. After incubation, the separation of bound signal generator (Ab$_F$-HRP from unbound was performed by addition of 0.65 g of GB-avidin into each tube, then incubating 10 minutes at 37° C. and finally washing with 4×1 ml of wash buffer (0.01M NaPi,pH 7.2). After washing, 0.3 ml of HRP substrate (TMB/urea H$_2$O$_2$) per tube was added and incubated at 37° C. for 5 minutes. Using a standard curve, constructed with the method described, thirty-nine patient samples were quantitated for digoxin concentration. The results obtained compared favorably with values generated by known radioimmune assays (RIAs).

Example 2: Heterogeneous enzyme-based immunoassay for total T$_3$

Preparation of Materials

A. Preparation of T$_3$-LC-F Conjugate

The reagent was prepared in three successive steps by preparing (1)F-NHS, (2) F-LC-NH$_2$, and (3) T$_3$-LC-F. The F-NHS and F-LC-NH$_2$ were prepared as described in Example 1.

A solution, containing 30.4 mg (0.05 mmoles) of triiodothyroformic acid, 50.35 mg (0.1 mmoles) F-LC-NH$_2$ and 19,2 mg (0.1 mmoles) EDAC in 1 mL of DMF/DMSO (4:1) solvent, was stirred overnight at room temperature in the dark. The T$_3$-LC-F and triiodothyroformic acid (if any left unreacted) were precipitated by adding 5 mL of D-H$_2$O, filtered, and the solvent discarded. The filtered material was resolubilized in a solvent system consisting of CH$_2$Cl$_2$: methanol: acetic acid (50:50:5) and was loaded onto a 1.5×20 cm silica gel column in the same solvent system. Under these conditions, triiodothyroformic acid moved ahead of T$_3$-LC-F conjugate, and the F-LC-NH$_2$ remained bound to the top of the column. The purity of the material was checked by TLC silica gel plates, using the solvent system described above. The solvents were removed from the purified material by rotary evaporation and the product was resolubilized into a minimum volume of methanol/DMF (70:30). The last step was performed to remove most of the silica gel, which may be solubilized and co-eluted with the product during the purification. The product was stored in methanol/DMF (70:30) solvent system at −20° C. The concentration of T$_3$-LC-F in the stock solution was determined by A$_{490}$ from a standard curve constructed using known amounts of 6-carboxy-fluorescein.

B. Preparation of Ab$_{T3}$-Biotin

Anti-T$_3$ antibodies were purified to the IgG fraction using immobilized Protein A. The antibody IgG's were biotinylated using biotin-LC-NHS (Ab:biotin-LC-NHS=1:25 molar ratio in the reaction mixture). The uncoupled biotin was removed by Sephadex-G25 column, and the Ab$_{T3}$-biotins were stored in 0.05M Na-Pi/pH=7.4 at 4° C. or frozen.

C. Coupling the Avidin to Glass Beads (GB)

The reagent was prepared by modifying the 0.5 mm-1.0 mm nonporous glass beads with 3-aminopropyltriethoxysilane to generate reactive amino groups on the surface of glass beads. The GB-NH$_2$ then was coated with CM-dextran using EDAC and finally succinylated to convert all of the amino groups into carboxyl groups. Avidin was coupled to the CM-dextran coated GB by EDAC chemistry. Finally, the avidin-labeled glass beads were coated with a solution containing 2.5% sucrose, 0.1% BSA. After drying the beads under reduced pressure, they were used in the assays.

Example 1 provides an alternative method for preparing the avidin coated glass beads.

D. Assay Working Solutions

1. Assay Buffer. 0.075M Sodium barbital, 0.2M NaCl, 0.002% thimerosal, 0.1% BSA, pH=8.6.

2. Releasing Reagent (RR). Assay buffer containing 1 mg/mL ANS, 5 mM EDTA, 0.5 mg/mL BGG, 0.5 mg/mL sheep IgG, 4% normal mouse serum was used to release the bound T$_3$ from serum proteins.

3. TMB/H$_2$O$_2$ HRP Substrate. Concentrated stock solutions were prepared as described in Example 1.

Assay Protocol

The assay was performed in 10×75 mm disposable glass tubes by the sequential addition of 50 μl of the commercially available standard or the unknown serum sample, 50 μl of 1.5 ng/ml T$_3$-LC-F in the releasing reagent, and 100 μl of a mixture of 80 ng/ml biotin-Ab$_{T3}$ and 1 μg/ml Ab$_F$-HRP conjugates. The assay mixtures were agitated in a vortex mixer and incubated at 37° C. for 15 minutes. After incubation, the separation of bound signal generator (Ab$_F$-HRP) from unbound was performed by the addition of 0.65 g of GB-avidin into each tube, incubating for 10 minutes at 37° C., and washing with 4×1 ml of wash buffer (0.01M NaPi, pH 7.2). After washing, 0.3 ml of HRP substrate (TMB/urea H$_2$0) per tube was added and incubated at 37° C. for 5 minutes. The reaction was stopped by adding 1 ml of 1N H$_3$PO$_4$ and the amount of color generated was measured at A$_{450}$. Using the standard curve, constructed using the method described above, 41 patient serum samples were quantitated for T$_3$ concentrations. The results obtained compared favorably with values generated by known radioimmune assays (RIAs).

Example 3: Heterogeneous enzyme-based immunoassay for detection of TSH
Preparation of materials
A. Preparation of Ab$_{TSH\beta}$ #1—Biotin Anti-TSH antibodies were either purified by immobilized Protein A to obtain the Ab IgG fraction or purchased pure from a commercial source. (BiosPacific, Menlo Park, Calif.; Cambridge Medical, Cambridge, Mass.) The Ab-biotin was prepared by mixing the Ab (1–3 mg/ml) in 0.1M NaPi, 0.2 m NaCl/p$_H$ 7.5) and sulfo-NHS-LC-Biotin. The sulfo-NHS-LC-Biotin was added in 3–5 aliquots over fifteen minutes and the reaction was allowed to run at room temperature for 1.5 hr. Uncoupled biotinylating reagent was removed by a Sephadex G-25 column. The molar ratio of Ab:Sulfo-NHS-LC-Biotin was 1:10, 1:20 and 1:40. The conjugate was stored in reaction buffer containing 0.001% thimerisol.

B. Preparation of Ab$_{TSH\beta}$ #2—F1

1. Preparation Of F-NHS: To 3.4 ml DMF containing 377.12 mg 6-carboxyfluorescein and 115 mg NHS was added 0.6 ml DMF containing 206.3 mg DCC. The mixture was stirred, overnight at room temperature. Dicycloxexylurea was removed by filtration. The F-NHS was checked by TLC on silica plates using dichloromethame:methanol:acetic acid=90:10:1. F-NHS was stored in DMF at −20° C.

2. Preparation of Ab$_{TSH\beta}$-F: Anti-TSH was purified by Protein A chromatography and dialyzed into 0.1M NaPi, 0.2 m NaCl, 5 mM EDTA pH 7.3. The Ab-F was prepared by mixing the Ab (1.5–2.0 mg/ml) with F-NHS in DMF and allowing the reaction to run for 1.5 hr. at room temperature. F-NHS:Ab ratios used were 12.5:1 and 25:1.

C. Preparation of the anti-fluorescein—HRP conjugate

Reagent was prepared as described in Example 1.

D. Assay Protocol

The protocol of the TSH assay consists of three parts: 1.) the binding reaction between assay components (biotin Ab$_{TSH1}$, TSH, A$_{TSH2}$-F and Ab$_F$-HRP) in solution phase; 2.) the separation of the complex from the unbound assay components by GB-Avidin; and 3.) addition of enzyme substrate and color generation.

The TSH assay is performed in 10×75 mm glass tubes. To 150 μl of human or bovine serum containing various amounts of TSH is added 20 μl buffer (0.01M NaPi 0.150M NaCl, 1.0% BSA, 0.1% Tween-20(monolaurate, Sigma Chemical Company) containing 200 ng Ab$_F$-HRP and 20 μl buffer containing 180 ng Ab$_{TSH1}$-biotin and Ab$_{TSH2}$-F. The assay tubes were agitated on a vortex mixer and incubated at 37° C. for 12.5 minutes. After incubation 0.65 g GB-avidin was added and incubation was allowed to continue for an additional 12.5 minutes. The beads were then washed 4 times with 1.0 ml of wash buffer (0.01M NaPi, 0.15M NaCl, 0.1% Tween, pH 7.4). After washing 0.2 ml of HRP substrates (TMB/H$_2$O$_2$) was added and color allowed to develop for 5 minutes. The reaction was stopped by the addition of 0.4 ml H$_3$PO$_4$. Samples were diluted to 1.0 ml total volume and the optical density at OD$_{450}$ was measured.

The above description and examples serve to fully disclose the mixture including preferred embodiments thereof. Modifications obvious to those of ordinary skill in the art are intended to be within the scope of the following claims.

What is claimed is:

1. A method for carrying out a separation in a liquid binding assay comprising:
   combining in an aqueous medium (a) a first member of a specific binding pair (sbp), and (b) a sample under conditions wherein analyte if present in said sample forms a complex with said first sbp member;
   incubating said first sbp member and said sample;
   adding ceramic or glass beads of said aqueous medium, to which are bound a second sbp member capable of directly or indirectly binding said first sbp member to form a matrix of beads within said aqueous medium, wherein the volume of said aqueous medium is no greater than that which will cover the matrix of beads;
   incubating said aqueous medium with said beads without shaking; and
   aspirating said aqueous medium from said beads by means of a tube inserted into said matrix of beads wherein the size of said beads is large enough to permit removal of said aqueous medium without aspiration of said beads.

2. The method of claim 1 wherein said first sbp member is an antibody.

3. The method of claim 2 wherein said antibody has biotin conjugated thereto.

4. The method of claim 1 wherein said first sbp member has an enzyme conjugated thereto.

5. The method of claim 4 wherein said enzyme is horseradish peroxidase.

6. The method of claim 4 wherein said enzyme is alkaline phosphatase.

7. The method of claim 4 wherein said first sbp member is a hapten.

8. The method of claim 1 wherein said matrix is comprised of 50 to 50,000 beads.

9. The method of claim 8 wherein said beads are non-porous and range in size from 0.2 to 2.5 mm.

10. The method of claim 1 wherein said second sbp member is avidin.

11. The method of claim 1 wherein after separation of said aqueous medium from said beads, said beads are combined with a wash solution and said wash solution is aspirated from said beads.

12. The method of claim 1 wherein said aspiration is carried out using a tube having one or more orifices, each orifice having a diameter smaller than the minimum diameter of the smallest bead.

13. In a method of carrying out a separation of a first specific binding pair (sbp) member from an aqueous medium wherein said first sbp member is bound to a solid phase and separated from said medium, the improvement comprises
   (a) combining in said aqueous medium ceramic or glass beads of a size from 0.2 to 2.5 mm in diameter to which are bound a second sbp member capable of binding said first sbp member to form a matrix of beads within said aqueous medium, wherein the volume of said aqueous medium is no greater than that which will cover the matrix of beads,
   (b) incubating said beads with said aqueous medium without shaking; and
   (c) aspirating said aqueous medium from said beads using an aspiration tube that can be inserted into said matrix of beads for separation of said beads from said medium.

14. The method of claim 13 wherein said aspiration tube has one or more orifices, each orifice having a diameter smaller than the minimum diameter of the smallest of said beads thereby providing a means to aspirate said aqueous medium without aspiration of said beads into said tube.

15. An assay method for the determination of an analyte in a sample suspected of containing the analyte wherein the analyte is an sbp member in an assay medium, and a labeled sbp member is separated from the assay medium in an amount related to the concentration of analyte present in the medium, which method comprises:

combining in an assay medium the sample and labeled sbp member;

incubating said assay medium;

adding to said medium a matrix comprised of ceramic or glass beads to which are bound an sbp member capable of directly or indirectly binding said labeled sbp member;

incubating said matrix with said assay medium containing said analyte and labeled sbp member wherein the volume of said assay medium is no greater than that which will cover said matrix and wherein said incubation of said matrix with said assay medium is conducted without shaking;

aspirating said assay medium from said beads using an aspiration tube having one or more orifices each of a diameter smaller that the minimum diameter of the smallest of said beads wherein said labeled sbp member bound to said beads is separated from said labeled sbp member that is not bound; and examining said beads for the presence of said labeled sbp member.

16. The method of claim 15 which further comprises combining said beads with an aqueous wash medium prior to examining said beads.

17. The method of claim 16 wherein examining said beads is done in the presence of said wash medium.

18. The method of claim 15 wherein said labeled sbp member is an sbp member having biotin conjugated thereto and said beads have avidin conjugated thereto.

19. The method of claim 15 wherein said label on said sbp member is a fluorescent agent.

20. The method of claim 15 wherein said beads have a diameter of from 0.2 to 2.5 mm.

21. In an assay for an analyte in a sample suspected of containing the analyte, which analyte is a member of a specific binding pair (sbp) consisting of a ligand and its complementary receptor, wherein the analyte binds to a labelled complementary sbp member in solution, and where said sbp member-analyte complex binds to the surface of a ceramic or glass bead matrix, said beads are bound to a specific binding pair member capable of binding said analyte wherein the volume of said solution is no greater than that which will cover the matrix of beads, and where said solution is separated from said complex bound to said beads, the improvement comprising incubating said solution with said bead matrix without shaking; and separating said solution from said complementary sbp member-analyte complex bound to said beads by inserting into said matrix an aspiration tube having one or more orifices each of a diameter smaller than the minimum diameter of the smallest of said beads.

22. The method of claim 21 wherein said complementary sbp member is labelled with a fluorescent agent.

23. The method of claim 22 wherein said beads are non-porous and have a diameter of from 0.2 to 2.5 mm.

24. The method of claim 22 wherein said beads have a diameter of from 0.5 to 1.5 mm.

25. The method of claim 23 wherein said beads have avidin bound to them.

26. A method for conducting an assay, which comprises:

a.) forming in an aqueous medium bound and free species of an analyte, wherein said bound species consists of said analyte bound to a first specific binding pair member;

b.) incubating said medium without agitation with a matrix of ceramic or glass beads to which are bound a second specific binding pair member capable of binding said bound or said free species wherein said medium is of a volume no greater than that required to cover said matrix, and wherein said incubation is performed without shaking;

c.) aspirating said medium from said beads by inserting into said matrix an aspiration tube having one or more orifices each of a diameter smaller that the minimum bead diameter; and d.) examining said beads for the presence of either said bound or said free species, bound to said second specific binding pair member.

27. The method of claim 26 wherein said beads are non-porous and have a diameter from 0.2 to 2.5 mm.

28. The method of claim 27 wherein said second specific binding pair member is avidin.

29. The method of claim 26 wherein said first specific binding pair member is a conjugate of an antibody complementary to said analyte and an enzyme.

30. The method of claim 29 wherein said enzyme is horseradish peroxidase.

31. A method for carrying out a separation in an assay, wherein a liquid medium is separated from beads, comprising:

combining in a liquid medium a first member of a specific binding pair (sbp) and a sample under conditions wherein analyte if present in the sample forms a complex with said first sbp member;

combining said liquid medium with a matrix of 50 to 50,000 non-porous ceramic or glass beads having a size of from 0.2 to 2.5 mm in diameter wherein said beads have bound thereto a second sbp member capable of directly or indirectly binding said first sbp member, wherein the volume of said liquid medium is no greater than that which will cover the matrix of beads;

incubating said liquid medium with said matrix without shaking; and separating said liquid medium from said beads by aspiration using an aspiration tube having one or more orifices each of a diameter smaller than the minimum diameter of the smallest of said beads such that the diameter of said beads is large enough to permit removal of said liquid medium without aspiration of said beads.

32. A method for carrying out a separation in a heterogeneous immunoassay comprising:

combining an aqueous medium containing a member of an antigen-antibody pair and a sample with a matrix consisting of non-porous ceramic of glass beads to which are bound a specific binding pair capable of directly or indirectly binding a member of said antigen-antibody pair, wherein the volume of said aqueous medium is no greater than that which will cover the matrix of beads;

incubating said aqueous medium with said matrix without shaking; and separating said aqueous medium from said beads by means of an aspiration tube wherein the minimum diameter of said beads is larger than the orifice of said aspiration tube thereby allowing removal of said aqueous medium while prohibiting aspiration of said beads.

33. The method of claim 32 wherein combination of said member of an antigen-antibody pair with said sample occurs under conditions wherein said analyte if present in said sample forms a complex with said member.

34. The method of claim 32 wherein the beads range in size from 0.2 to 2.5 mm.

35. A method for carrying out a separation in a binding assay comprising:

combining an aqueous medium containing a first member of a specific binding pair (sbp) and a matrix comprised of ceramic or glass beads to which are bound a second sbp member, wherein said first member binds directly or indirectly to said second member, and wherein the volume of said aqueous medium is no greater than that which will cover the matrix of beads;

incubating said medium with said matrix without shaking; and aspirating said aqueous medium by means of a tube inserted in said matrix wherein the size of said beads comprising said matrix is large enough to permit removal of said aqueous medium without aspiration of said beads.

36. The method of claim 35 wherein said beads are non-porous and range in size from 0.2 to 2.5 mm.

37. The method of claim 35 wherein said liquid medium can be aspirated from said beads by means of an aspiration tube having one or more orifices each of a diameter smaller than the minimum bead diameter.

38. The method of claim 35 wherein said matrix is comprised of from 50 to 50,000 non-porous glass beads.

39. The method of claim 35 wherein said first member is bound to a signal producing system.

40. The method of claim 39 wherein said signal producing system is a horseradish peroxidase enzyme system.

* * * * *